United States Patent [19]

Rule

[11] Patent Number: 4,788,355

[45] Date of Patent: Nov. 29, 1988

[54] OXYIODINATION CATALYST

[75] Inventor: Mark Rule, Kingsport, Tenn.

[73] Assignee: Eastman Kodak Company, Rochester, N.Y.

[21] Appl. No.: 109,029

[22] Filed: Oct. 16, 1987

[51] Int. Cl.$^4$ ..................... C07C 17/152; C07C 17/15
[52] U.S. Cl. ..................................... 570/203; 570/208
[58] Field of Search ................ 570/206, 208, 203, 204

[56] References Cited

U.S. PATENT DOCUMENTS

| 3,363,010 | 11/1968 | Schwarzenbek | 570/203 |
| 3,600,331 | 8/1971 | Ingwalson | 570/203 |
| 3,644,542 | 2/1972 | Prahl et al. | 570/203 |
| 4,240,987 | 12/1980 | Martin et al. | 570/206 |
| 4,391,785 | 7/1983 | Rosinski et al. | 502/77 |
| 4,513,092 | 4/1985 | Chu et al. | 502/77 |

FOREIGN PATENT DOCUMENTS

| 0181790 | 5/1986 | European Pat. Off. | 570/206 |
| 183579 | 6/1986 | European Pat. Off. | |
| 77631 | 5/1982 | Japan | 570/206 |
| 59-219241 | 12/1984 | Japan | |
| 5877830 | 5/1985 | Japan | |
| 159496 | 12/1963 | U.S.S.R. | 570/206 |
| 453392 | 1/1975 | U.S.S.R. | |

OTHER PUBLICATIONS

Groggins, "Unit Processes in Organic Chemistry", Fifth Ed., (1958), McGraw–Hill Book Co., Inc., p. 262.
Journal of the American Chemical Society, 39, 437, (1917).
Journal of Chemical Education, 48, 508, (1971).
Bulletin of Chemical Society of Japan, 47, 147, (1974).

Primary Examiner—Werren B. Lone
Attorney, Agent, or Firm—Charles R. Martin; William P. Heath, Jr.

[57] ABSTRACT

Disclosed is a process for iodinating an aromatic compound over a zeolite catalyst containing a deactivation modifier selected from the group consisting of ions or salts of hydrogen, copper, zinc, cadmium, silver and mercury.

9 Claims, No Drawings

OXYIODINATION CATALYST

BACKGROUND OF THE INVENTION

1. Field of the Invention

The present invention relates to a process for iodinating aromatic compounds, in particular, a process for iodinating aromatic feeds containing alkyl aromatics with catalysts having a decreased susceptibility to deactivation.

2. Discussion of Background

It has long been desired to be able to derivatize aromatic compounds and in particular condensed ring aromatic compounds in commercially attractive quantities since many of these compounds possess properties which would fill long sought needs. In particular, substituted benzene and naphthalene carboxylic acids or esters are particularly desired for use in the manufacture of polyesters which would have excellent properties when fabricated into films, bottles or coatings. However, known techniques for producing these carboxylic acids and esters are very expensive and impractical for commercial exploitation.

Synthesis of iodobenzene starting from benzene and iodine is usually carried out in the liquid phase in the presence of an oxidative agent, preferably nitric acid. Such techniques have been described in the literature and the in particular in Japanese 58/77830, U.S.S.R. Pat. No. 453392 and by Data and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 48, 508, (1971). The use of metal halogenides to catalyze iodination has been suggested by Uemura, Noe, and Okano in the *Bulletin of Chemical Society of Japan*, 47, 147, (1974). The concept of direct iodination of benzene in the gas phase over the zeolite 13X has been suggested in Japanese Patent Publication 82/77631 in the absence of any oxidizing agent.

Ishida and Chono in Japanese Kokai No. 59/219241 have suggested a technique for oxyiodinating benzene over a very acidic zeolite catalyst having a silica to alumina ($SiO_2/Al_2O_3$) ratio of greater than 10. In this technique benzene is reacted with iodine in the presence of oxygen to produce iodinated benzene. According to this disclosure approximately 96% of the benzene which is converted is converted to the iodinated form. However, the remaining benzene is oxidized to carbon dioxide and other combustion products resulting in the loss of valuable starting material.

Paparatto and Saetti disclosed in European Patent Application Nos. 181,790 and 183,579 techniques for oxyiodination of benzene over zeolite catalysts. European Patent Application No. 181,790 suggests the use of ZSM-5 and ZSM-11 type zeolites which has been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type of Y type of zeolite in non-acid form. According to 183,579 the X or Y zeolites have to be used in the form exchanged with monovalent, bivalent or trivalent cations and in particular with alkaline or rare earth cations. The techniques of 181,790 and 183,579 prepare the mono-iodobenzene in selectivities in excess of 90% and only distinctly minor amounts of the diiodobenzene compounds.

A common deficiency of zeolite catalyst systems such as those noted above is the susceptibility of the catalyst to deactivation when the aromatic feed material contains alkyl aromatics and in particular methyl aromatic compounds. Typically, the deactivation effect becomes more pronounced as the molecular weight of the alkyl aromatic compound increases. It is speculated that this deactivation arises from the oxidation of the alkyl aromatic compound to an aromatic carboxylic acid which is relatively nonvolatile and remains on the catalyst blocking the catalyst sites and/or pore openings.

Since high-purity aromatic feeds are more costly than the corresponding lower purity feed, and the impurities in the aromatic feed are commonly alkyl aromatics, there is a need for an iodination process which utilizes catalyst which are less susceptible to deactivation when the aromatic feed material contains alkyl aromatic compounds.

SUMMARY OF THE INVENTION

Accordingly, one object of the present invention is to provide a technique for catalytically iodinating aromatic compounds contaminated with alkyl aromatics without substantial deactivation of the catalyst.

Another object of the invention is the process for iodinating substituted or unsubstituted benzenes or napthalenes over a zeolite catalyst with substantially no deactivation of the catalyst.

These an other objects of the present invention which will become apparent from the following specification have been achieved by the present process which comprises reacting a source of iodine with an aromatic compound in the presence of oxygen over a zeolite catalyst containing an amount of a modifier effective to substantially prevent deactivation of said catalyst by alkyl aromatic compounds, said modifier being at least one modifier selected from the group consisting of hydrogen, copper, zinc, cadmium, silver, and mercury ions, or salts thereof.

DESCRIPTION OF THE PREFERRED EMBODIMENTS

The aromatic compounds which can be utilized in practice of the present invention are essentially any substituted or unsubstituted aromatic compounds. Here a substituent is considered to be a terminal group replacing hydrogen on the parent aromatic species. Suitable aromatic compounds include hydrocarbon aromatics, nitrogen-containing aromatics, oxygen-containing aromatics and sulfur-containing aromatics. Typical hydrocarbon aromatics include benzene and biphenyl; condensed ring aromatics such as naphthalene and anthracene; sulfur-containing aromatics including thiphene and benzothiophene; nitrogen-containing aromatics including pyridine and benzopyridine; and oxygen-containing aromatics including furan and benzofuran. Other parent aromatics include diaryl sulfones, diaryl ethers, diaryl carbonyls, diaryl sulfides and the like. Preferred parent aromatics are benzenes, biphenyls and naphthalenes.

Substituents on the aromatic compounds which are suitable for the process of the present invention include fluoro, chloro, bromo, iodo, hydroxy, and cyano.

Aromatic compounds which are substituted by alkyl groups may be present in the aromatic starting material since the catalyst of the present invention has a increased tolerance to the presence of alkyl aromatics. The increased tolerance of the present catalyst to the presence of alkyl aromatic compounds is achieved by modifying a zeolite catalyst with low levels of hydrogen, copper, zinc, cadmium, silver and/or mercury ions or their salts. While not being bound to any particular theory, it is believed that these modifiers work by promoting the decarboxylation of the aromatic carboxylic acid which is formed by initial oxidation of the alkyl aromatics. The modifiers are incorporated into the catalysts by standard ion exchange techniques.

The catalysts utilized in the present technique are generally characterized by containing non-acid sites, and more preferably basic sites. The most preferred catalyst for use in the present invention are zeolites in the non-acid form. The zeolites which are chosen must have a pore size at least equal to about the apparent size of the molecule of the substituted aromatic ring compound being reacted. Benzene as well as naphthalene have apparent ring sizes of about 6 Å and this the lower limit on the pore size of the zeolite catalyst which is useful. If the aromatic compound cannot enter into the pore on the zeolite catalyst then only very little conversion of the aromatic compounds will occur. Further, if the zeolite is in the acid form, excessive combustion or oxidation of the aromatic compound will occur which is not preferred. Hence, the preferred zeolites are all in the non-acid form and all contain a pore size of about 6 Å or larger.

Iodination processes utilizing both acidic and non-acidic catalysts are disclosed in copending application Ser. Nos. 912,806, filed Sept. 9, 1986; 029,896, filed Mar. 25, 1987; 029,959, filed Mar. 25, 1987; 029,897, filed Mar. 25, 1987; 029,898, filed Mar. 25, 1987; 070,249, filed July 6, 1987; and 109,030, filed Aug. 18, 1987. Catalyst systems which perform a transoxyiodination are disclosed in copending application Ser. Nos. 029,899, filed Mar. 25, 1987; 029,956, filed Mar. 25, 1987, and 029,949, filed Mar. 25, 1987. The disclosures of these copending applications are incorporated herein by reference for a more complete description of these catalysts and iodination processes.

The type of zeolite which is utilized is not critical so long as an effective amount of a modifier, preferably 0.01–5.0 wt. %, more preferably 0.1–3.0 wt. % of the catalyst is hydrogen, copper, zinc, cadmium, silver, and/or mercury ions and the pore size is greater than about 6 Å. In general, the reaction rate is a function of silicon to aluminum ratio in the zeolite, since aluminum is part of the active site. It is preferred to use zeolites of with a silicon (as Si) to aluminum (as Al) ratio of 10:1 or less, more particularly 5:1 or less, still more preferred are those zeolites having a silicon to aluminum ratio of 3:1 or less with the most preferred type having a silicon to aluminum ratio of 1.5 or less. Particular types of zeolites which have proven useful are the X and Y types. The Y type zeolite generally has a silicon to aluminum ratio of about 1.5 to 1 to 3:1. The X type zeolite is generally considered to have a silicon to aluminum ratio of about 1:1 to 1.5:1. The X type zeolite exhibits more sensitivity to the counter ion than the Y type does. That is, the selectivity of this X type zeolite to the production of specific mono, di or triiodinated aromatic compounds can be altered more successfully with the selection of the appropriate counter ions than can the Y type. While not being bound to any particular theory it is believed that the counter ion affects the selectivity by altering the shape of the active site thereby increasing or decreasing the selectivity of the catalyst for any particular isomer as compared with the standard sodium form. As a number of cations at the active site decreases their influence in the shape of the pore decreases and thus selectivity decreases. Thus, when one desires to produce a particular isomer high alumina content zeolites are preferred. Especially preferred catalysts are those described in the copending applications noted above.

Most of the commercially available zeolites are in the sodium form. The counter ion is easily changed in the zeolite by simple ion exchange and is well known to those skilled in the art. This is generally accomplished by contacting in an aqueous medium a salt of desired modifier ion and the zeolite. The period of time over which the contact is conducted and a number of times the ion exchange processs is performed is dependent upon the degree of replacement which is desired.

Other compounds which have been proven useful as catalysts in the present invention are non-zeolitic and are characterized as containing alkali or alkaline earth salts. Typical catalysts include magnesium oxide on silica, calcium aluminate, magnesium aluminate, potassium chloride or alumina, sodium sulfate on silica and the like. These catalysts may be supported or unsupported or bound together with a binder to form a shaped particle. Typical supports and binders include silica, aluminum various clays and the like. In general, any material not containing acid sites can be utilized as the catalyst support. These non-zeolite catalysts generally do not exhibit the selectivity of the zeolite catalyst when producing polyiodinated products.

The temperature which the reaction is to be conducted is not critical and can be any temperature at which when the aromatic compound is fluid. The maximum temperature at which the process can be carried out is that at which combustion of the aromatic compound occurs. Generally, temperatures of from about 100° to 500° C. have been found satisfactory, with temperatures of from 200° to 400° C. being preferred, more preferably from about 200° to 350° C.

The pressure which the process is conducted is not critical and can range from subatmospheric to superatmospheric. The utilization of elevated pressures in the gas phase process may be preferred so as to minimize equipment size. In general, pressures from atmospheric to 600 psig have proven satisfactory although higher or lower pressures can be utilized. The reaction may be conducted in either the liquid or the vapor phase.

The molecular oxygen can be introduced as pure oxygen, air or oxygen diluted with any other inert material such as carbon dioxide or water vapor. Essentially oxygen from any convenient source may be utilized. The purpose of the oxygen is to regenerate the active site on the catalyst to its active form once the iodination reaction has occurred. Thus, the amount of oxygen present during the reaction is not critical. However, it is preferred that at least $\frac{1}{2}$ mole of oxygen be used for every mole of iodine. The molar ratio of iodine to aromatic compound which is to be reacted is largely determined by whether one desires to produce a monoiodinated aromatic product or polyiodinated aromatic product. Stoichiometrically, ½ mole of iodine reacts with 1 mole of aromatic compound to produce the monoiodinated form. Similarly, on a stoichiometric basis 1 mole of iodine is required to convert 1 mole of aromatic compound to the diiodionated form. Greater or lesser quantities of iodine can be utilized as the artisan may desire. In general, it is desired to run the process to obtain as close to 100% conversion of the iodine as a practical so as to simplify the purification steps in the recovery of any unreacted iodine. Suggested mole ratios of aromatic compound to iodine to oxygen are from 1:0.5:.25 to about 1:2:3.

Essentially any source of iodine may be employed including elemental iodine ($I_2$), hydroiodic acid in gaseous form, or alkyl iodides, preferably lower alkyl iodides. Furthermore, mixtures of these materials may be used as the source of iodine.

It is anticipated that he present process would be carried out continuously by the continuous addition of iodine, oxygen and aromatic compound to the reactor; however, the process can be carried out on a batch or semi batch process as desired. Further, aromatic compound of iodine can be reacted over the catalyst to produce the iodinated product, the addition of the aromatic compound and iodine then being terminated and oxygen then added to the reactor to regenerate catalyst to its active form and then the process commenced again. Alternatively, in a continuous process it is possible to utilize two reactants, circulating the catalyst between them. In the first reactor the iodine and aromatic compound would be added and reacted to form the iodinated compound. The catalyst would then be circulated to the second reactor where it would be contacted with oxygen to be regenerated and then recycled to the first reactor to catalyze additional reactions of aromatic compound with iodine.

The space velocity of the process is not critical and may be readily selected by the artisan. Gas hourly space velocity is between 10 and 50,000, preferably between 100 and 20,000 liters per hour of reagents per liter of active zeolite have proven satisfactory.

When reagent grade aromatics, such as benzene, naphthalene, or biphenyl are the aromatic feed the catalyst is proven to have an extremely long life and degrades only slowly with time. The degradation of the catalyst is believed to be caused by the decomposition of very small quantities of the aromatic compound which deposits small quantities of carbon on the active sites thereby degrading the catalyst activity. When the reaction conditions are selected such that none of the aromatic starting material is oxidized, the life of the catalyst is essentially indefinite. However, when the catalyst becomes deactivated reactivation is simple. An excellent regeneration technique comprises passing air or oxygen over the catalyst for several hours at elevated temperatures. Typically the temperature is above 400° C. although higher or lower temperatures have proven equally satisfactory. The temperature need only be high enough so as to ensure combustion of the carbon deposit on the catalyst. When pure oxygen is employed lower temperatures can be utilized, while when air is employed temperatures on the order of about 400° C. have proven satisfactory.

When the aromatic feed contains alkyl aromatic impurities, the catalyst life is severely affected. For example, with reagent grade benzene as feed, a catalyst life of over 1,000 hours is observed without significant deactivation. When the benzene feed contains 1.0 wt. % p-xylene, complete deactivation occurs in less than four hours under the same conditions. With reagent grade naphthalene feed catalyst life in excess of 400 hours can be achieved, whereas naphthalene containing 0.5 wt. % 2-methyl naphthalene deactivates the catalyst in less than three hours.

This deactivation is not irreversible, since the catalyst can be regenerated to full activity as described above. Moreover, at lower levels of alkyl aromatic impurities the catalyst will not be completely deactivated, but will possess a lower steady-state activity than in the absence of the alkylaromatic.

It is believed that this deactivation arises from oxidation of the alkyl aromatic to an aromatic carboxylic acid, which is nonvolatile and blocks the catalyst site or pore openings until decarboxylation occurs, yielding a volitle aromatic hydrocarbon and carbon dioxide. If the rate of this decarboxylation could be increased, the catalyst could accept greater amounts of alkyl aromatics in the feed without deactivating.

I have now found that the addition of low levels of certain additives to oxyiodination catalyst substantially improve their steady-state activity when the aromatic feed contains low levels of alkyl aromatics. The additives which are active are thought to promote the decarboxylation of aromatic carboxylic acids formed on the catalyst.

The following examples are presented to illustrate the present invention but are not intended in any way to limit the scope of the invention which is defined by the appended claims.

EXAMPLES

The following examples demonstrate the effectiveness of the modifier ions in promoting tolerance of alkyl aromatic starting materials. In these examples, 100 grams of the modified catalyst was tested at 300° C. with the feed of 3.0 mmol/min naphthalene containing 0.05% 2-methyl naphthalene, 2.25 mmol/min iodine, and 300 mL/min air. The results tabulated below are in % iodine conversion and mol % diodonaphthalenes (DIN) in the product. The base catalyst in all cases was K-X 16–40 mesh beads, which operated at greater than 95% iodine conversion under the above conditions when the feed was reagent grade naphthalene.

TABLE 1

| Promoter | Weight % | % I2 Conversion | % DIN's |
|---|---|---|---|
| — | — | 15.4 | 1.1 |
| CuCl2 | 1.0 | 28.3 | 5.4 |
| Ce(NO3)3 | 0.5 | 11.5 | 0.0 |
| Cu(OAc)2 | 2.5 | 63.4 | 19.2 |
| ZnCl2 | 1.5 | 84.3 | 39.0 |
| CdCl2 | 2.5 | 80.9 | 40.6 |
| CoCl2 | 1.0 | 29.0 | 4.2 |
| HCl (37%) | 1.0 | 91.3 | 45.1 |
| HCl (37%) | 0.5 | 44.4 | 8.8 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for preparation of mono and diiodo benzene, naphthalene or diphenyl by iodinating a fluoro, chloro, bromo, iodo, hydroxy, or cyclo substituted benzene, naphthalene or diphenyl, which comprises reacting, at a temperature in the range of 100° to 500° C., a source of iodine with the substituted benzene, naphthalene or diphenyl in the presence of molecular oxygen over a zeolite catalyst with a pore size of 6 angstroms or greater and greater than ten percent of the exchangeable cations being alkali, alkaline earth or rare earth metal cations, wherein said catalyst contains an amount of a modifier effective to substantially prevent deactivation of said catalyst by alkyl substituted aromatic compounds, said modifier being selected from the group consisting of hydrogen, copper, zinc, cadmium, silver, and mercury ions or salts thereof.

2. The process of claim 1, wherein said modified comprises 0.01 to 5.0 weight % of said catalyst.

3. The process of claim 1, wherein said modifier comprises 0.1 to 3.0 weight % of said catalyst.

4. The process of claim 1, wherein said iodinating reaction is conducted at a temperature of about 200° to 400° C.

5. The process of claim 1, wherein said source of molecular oxygen is pure oxygen, air or oxygen diluted with an inert material.

6. The process of claim 5, wherein said source of oxygen is air.

7. The process of claim 1, wherein said source of iodine is elemental iodine, hydroiodic acid, or alkyl iodides.

8. The process of claim 7, wherein said source of iodine is elemental iodine.

9. A process for iodinating benzene or naphthalene, which comprises reacting, at a temperature in the range of 200° to 400° C., a source of iodine with benzene or naphthalene in the presence of air over a zeolite catalyst, wherein said catalyst contains 0.01 to 5.0 weight % of a modifier effective to substantially prevent deactivation of said catalyst by alkyl substituted aromatic compounds, said modifier being selected from the group consisting of hydrogen, copper, zinc, cadmium, silver, and mercury ions or salts thereof.

* * * * *